(12) United States Patent
Bédard et al.

(10) Patent No.: US 7,815,689 B2
(45) Date of Patent: Oct. 19, 2010

(54) INSTRUMENTED PROSTHETIC FOOT

(75) Inventors: Stéphane Bédard, Saint-Augustin-de-Desmaues (CA); Pierre-Ollvier Roy, Sainte-Foy (CA)

(73) Assignee: Victhom Human Bionics Inc., Quebec (CA)

( * ) Notice: Subject to any disclaimer, the term of this patent is extended or adjusted under 35 U.S.C. 154(b) by 167 days.

(21) Appl. No.: 12/260,479

(22) Filed: Oct. 29, 2008

(65) Prior Publication Data
US 2009/0143870 A1 Jun. 4, 2009

Related U.S. Application Data

(63) Continuation-in-part of application No. 10/715,989, filed on Nov. 18, 2003, now abandoned.

(51) Int. Cl.
*A61F 2/68* (2006.01)
(52) U.S. Cl. .......................... 623/53; 623/24
(58) Field of Classification Search .................. 623/24, 623/47–56
See application file for complete search history.

(56) References Cited

U.S. PATENT DOCUMENTS

| | | | |
|---|---|---|---|
| 4,030,141 A | 6/1977 | Graupe |
| 4,179,759 A | 12/1979 | Smith |
| 4,387,472 A | 6/1983 | Wilson |
| 4,521,924 A | 6/1985 | Jacobsen et al. |
| 4,558,704 A | 12/1985 | Petrofsky |
| 4,994,086 A | 2/1991 | Edwards et al. |
| 5,062,856 A | 11/1991 | Sawamura et al. |
| 5,062,857 A | 11/1991 | Barringer et al. |
| 5,133,773 A | 7/1992 | Sawamura et al. |
| 5,133,774 A | 7/1992 | Sawamura et al. |
| 5,252,102 A | 10/1993 | Singer et al. |
| 5,383,939 A | 1/1995 | James |
| 5,443,528 A | 8/1995 | Allen |
| 5,571,205 A | 11/1996 | James |
| 5,571,213 A | 11/1996 | Allen |
| 5,650,704 A | 7/1997 | Pratt et al. |
| 5,704,946 A | 1/1998 | Greene |

(Continued)

FOREIGN PATENT DOCUMENTS

DE 42 29 330 3/1994

(Continued)

OTHER PUBLICATIONS

Dietl, H., Der Einsatz von Elektronik bei Prothesen zur Versorgung der unteren Extremitat, Med. Orth. Tech. 117 (1997) 31-35.

(Continued)

*Primary Examiner*—William H Matthews
(74) *Attorney, Agent, or Firm*—Knobbe, Martens, Olson & Bear LLP

(57) ABSTRACT

The present invention discloses an instrumented prosthetic foot for use with an actuated leg prosthesis controlled by a controller, the instrumented prosthetic foot comprising a connector to connect the instrumented prosthetic foot to the leg prosthesis, an ankle structure connected to the connector, a ground engaging member connected to the ankle, at least one sensor for detecting changes in weight distribution along the foot, and an interface for transmitting signals from the sensor to the controller.

6 Claims, 15 Drawing Sheets

U.S. PATENT DOCUMENTS

| | | | |
|---|---|---|---|
| 5,746,774 | A | 5/1998 | Kramer et al. |
| 5,779,735 | A | 7/1998 | Molino |
| 5,888,212 | A | 3/1999 | Petrofsky et al. |
| 5,888,213 | A | 3/1999 | Sears et al. |
| 5,888,246 | A | 3/1999 | Gow |
| 5,893,891 | A | 4/1999 | Zahedi |
| 5,895,430 | A | 4/1999 | O'Connor |
| 6,007,582 | A | 12/1999 | May |
| 6,091,977 | A | 7/2000 | Tarjan et al. |
| 6,113,642 | A | 9/2000 | Petrofsky et al. |
| 6,129,766 | A | 10/2000 | Johnson et al. |
| 6,361,570 | B1 | 3/2002 | Gow |
| 6,423,098 | B1 | 7/2002 | Biedermann |
| 6,425,925 | B1 | 7/2002 | Gundai |
| 6,443,993 | B1 | 9/2002 | Koniuk |
| 6,443,995 | B1 | 9/2002 | Townsend et al. |
| 6,494,039 | B2 | 12/2002 | Pratt et al. |
| 6,537,322 | B1 | 3/2003 | Johnson et al. |
| 6,764,520 | B2 | 7/2004 | Bedard |
| 7,147,667 | B2 | 12/2006 | Bedard |
| 2001/0029400 | A1 | 10/2001 | Deffenbaugh et al. |
| 2002/0052663 | A1 | 5/2002 | Herr et al. |
| 2002/0183803 | A1 | 12/2002 | Fang et al. |
| 2002/0198604 | A1 | 12/2002 | Schulam et al. |
| 2003/0029247 | A1 | 2/2003 | Biedermann |
| 2003/0120353 | A1 | 6/2003 | Christensen |
| 2004/0064195 | A1 | 4/2004 | Herr |
| 2004/0111163 | A1 | 6/2004 | Bedard et al. |
| 2004/0193286 | A1 | 9/2004 | Grundai |
| 2006/0249315 | A1 | 11/2006 | Herr et al. |
| 2007/0016329 | A1 | 1/2007 | Herr et al. |
| 2007/0043449 | A1 | 2/2007 | Herr et al. |
| 2007/0123997 | A1 | 5/2007 | Herr et al. |
| 2007/0162152 | A1 | 7/2007 | Herr et al. |

FOREIGN PATENT DOCUMENTS

| | | |
|---|---|---|
| DE | 195 21 464 | 6/1995 |
| EP | 0 549 855 | 7/1993 |
| EP | 1 166 726 | 1/2002 |
| EP | 1 169 982 | 1/2002 |
| FR | 2 623 086 | 5/1989 |
| FR | 2 293 185 | 7/1996 |
| GB | 2 201 260 | 8/1988 |
| GB | 2 260 495 | 4/1993 |
| GB | 2 302 949 | 2/1997 |
| JP | 11056885 | 3/1999 |
| JP | 2001277175 | 10/2001 |
| JP | 2002-191654 | 7/2002 |
| WO | WO 96/41599 | 12/1996 |
| WO | WO 98/25552 | 6/1998 |
| WO | WO 99/08621 | 2/1999 |
| WO | WO 99/29272 | 6/1999 |
| WO | WO 00/38599 | 7/2000 |
| WO | WO 0172245 | 10/2001 |
| WO | WO 2004/017871 | 3/2004 |

OTHER PUBLICATIONS

Flowers et al., Journal of Biomedical Engineering: Transactions of the ASME; Feb. 1977, pp. 3-8.

US 7,815,689 B2

INSTRUMENTED PROSTHETIC FOOT

CROSS REFERENCE TO RELATED APPLICATIONS

This application is a continuation-in-part of U.S. application Ser. No. 10/715,989, filed on Nov. 18, 2003, now abandoned the contents of which are incorporated herein by reference.

TECHNICAL FIELD

The present invention relates to a prosthetic foot for use with a control system and/or a method for controlling an actuated leg prosthesis.

BACKGROUND

As is well known to control engineers, the automation of complex mechanical systems is not something easy to achieve. Among such systems, conventional powered artificial limbs are notorious for having control problems. These conventional prostheses are equipped with basic controllers that artificially mobilize the joints without any interaction from the amputee and are only capable of generating basic motions. Such basic controllers do not take into consideration the dynamic conditions of the working environment, regardless the fact that the prosthesis is required to generate appropriate control within a practical application. They are generally lacking in predictive control strategies necessary to anticipate the artificial limb's response as well as lacking in adaptive regulation enabling the adjustment of the control parameters to the dynamics of the prosthesis. Because human limb mobility is a complex process including voluntary, reflex and random events at the same time, conventional prostheses do not have the capability to interact simultaneously with the human body and the external environment in order to have minimal appropriate functioning.

Accordingly, it is an object of the present application to obviate or mitigate some or all of the above disadvantages.

SUMMARY

According to the present invention, there is provided an instrumented prosthetic foot for use with an actuated leg prosthesis controlled by a controller, the instrumented prosthetic foot comprising a connector to connect the instrumented prosthetic foot to the leg prosthesis, an ankle structure connected to the connector, a ground engaging member connected to the ankle, at least one sensor for detecting changes in weight distribution along the foot, and an interface for transmitting signals from the sensor to the controller.

BRIEF DESCRIPTION OF THE FIGURES

Embodiments of the invention will be described by way of example only with reference to the accompanying drawings, in which.

DETAILED DESCRIPTION

The appended figures show a instrumented prosthetic foot (20) having sensors (22A, 22B) for use, in cooperation with possible additional sensors (24A, 24B, 26), with a control system (100) for controlling a prosthesis (14) having an actuating mechanism (16). It should be understood that the present invention is not limited to the illustrated implementation since various changes and modifications may be effected herein without departing from the scope of the appended claims.

Figure 1:
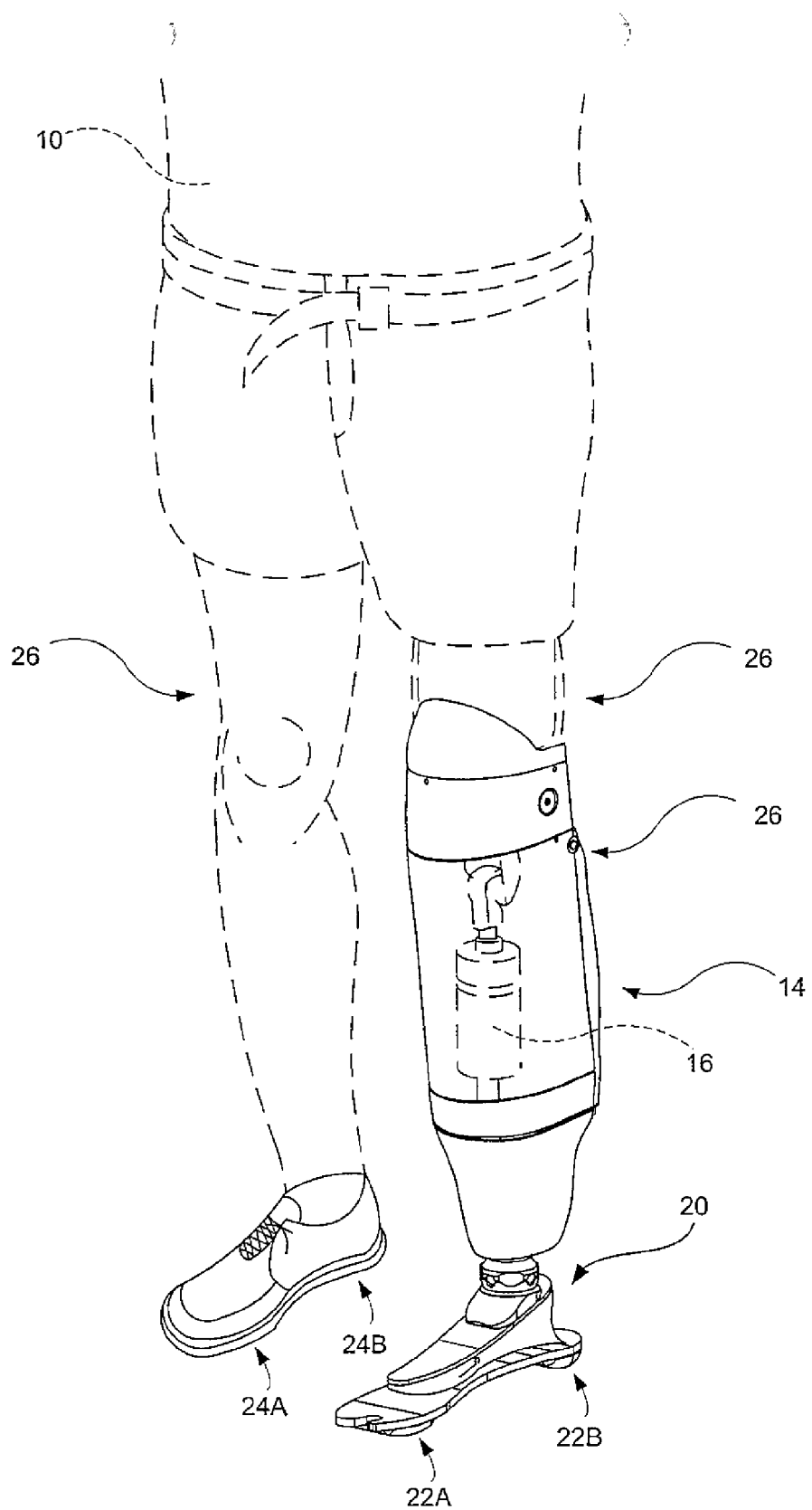
FIG. 1 shows the lower body of an individual provided with a prosthesis and an instrumented prosthetic foot on one side and having a healthy leg on the other side.

Referring therefore to FIG. 1 an individual (10) has a pair of legs (26) and (28), one of which, (26), is amputated above the knee. A prosthesis (14) is attached to the leg (26) and includes an actuating mechanism (16), which may be either passive or active. An instrumented prosthetic foot (20) is attached to the prosthesis (14) and includes sensors (22A, 22B). Additional sensors (24A, 24B) are located on the healthy foot and additional sensors (26) located on the individual (10) and/or the prosthesis (14). A passive actuating mechanism may be generally defined as an electro-mechanical component that only absorbs mechanical energy in order to modify dynamics of mechanical joints of the prosthesis, while an active actuating mechanism may be generally defined as an electro-mechanical component that absorbs and supplies mechanical energy in order to set dynamics of mechanical joints of the prosthesis.

An example of a passive actuating mechanism is described in U.S. patent application Ser. No. 09/767,367, filed Jan. 22, 2001, entitled "ELECTRONICALLY CONTROLLED PROSTHETIC KNEE". Examples of active actuating mechanisms are described in U.S. patent application Ser. No. 10/463,495 filed Jun. 17, 2003, entitled "ACTUATED PROSTHESIS FOR ABOVE-KNEE AMPUTEES", by Stéphane Bédard et al., the entire disclosure of which is hereby incorporated by reference herein.

Figure 2:
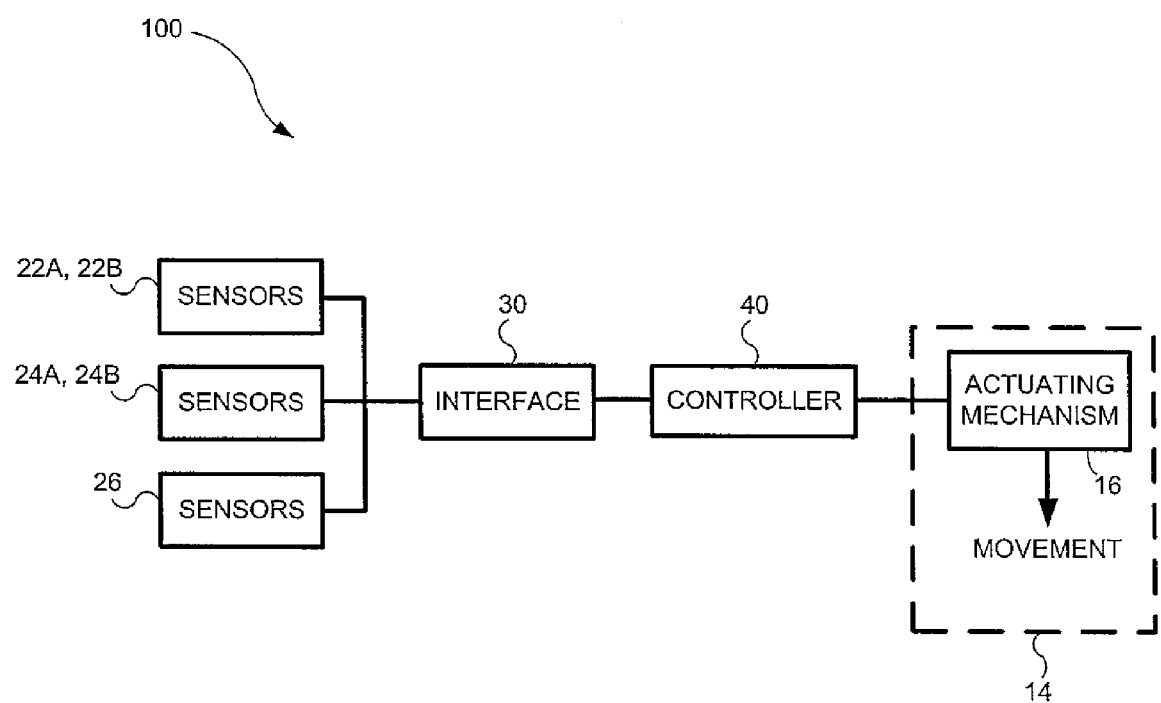
FIG. 2 is a block diagram showing a control system for a prosthesis having an actuating mechanism.

The prosthesis (14) is controlled, as shown schematically in FIG. 2, by a basic control system (100) comprising sensors (22A, 22B, 24A, 24B, 26), connected through an interface (30) to a controller (40). The controller (40) provides signals to an actuating mechanism (16) in the prosthesis (14), such as shown in FIG. 1. The purpose of the control system (100) is to provide the required signals for controlling the actuating mechanism (16). To do so, the control system (100) is interfaced with the amputee (10) using sensors (22A, 22B, 24A, 24B, 26) to ensure proper coordination between the amputee (10) and the movements of the prosthesis (14). The sensors (22A, 22B, 24A, 24B, 26) capture information, in real time, about the dynamics of the amputee's movement and provide that information to the controller (40) via the interface (30). The controller (40) then uses the information to determine the resistance to be applied to a joint, in the case of a passive actuating mechanism, or the joint trajectories and the required angular force or torque that must be applied by a joint, in the case of an active actuating mechanism, in order to provide coordinated movements.

The sensors (22A, 22B, 24A, 24B, 26) may include myoelectric sensors, neuro-sensors, kinematic sensors, kinetic sensors, strain gauges or plantar pressure sensors. Myoelectric sensors are electrodes used to measure the internal or the external myoelectrical activity of skeletal muscles. Neuro-sensors are electrodes used to measure the summation of one or more action potentials of peripheral nerves. Kinematic sensors are used to measure the position of articulated joints, the mobility speed or acceleration of lower extremities. Kinetic sensors are used to measure angular forces at articulated joints or reaction forces of lower extremities. Strain gages are used to measure the strain forces at a specific underfoot area. Plantar pressure sensors are used to measure the vertical plantar pressure of a specific underfoot area. Of course, additional types of sensors which provide various information about dynamics of human locomotion may be used. For a given application, the use of sensors (22A, 22B, 24A, 24B, 26) is not restricted to a specific type of sensor, multiple types of sensors in various combinations may be used.

As illustrated in FIG. 1, the sensors (22A, 22B) may comprise localized plantar pressure sensors located at spaced locations on the prosthetic foot (20) to measure the vertical plantar pressure of a specific underfoot area. Similarly, the plantar pressure sensors (24A, 24B) located on the side of the healthy foot may be provided at spaced locations in a custom-made insole, preferably in the form of a standard orthopedic insole, that is modified to embed the two sensors (24A, 24B) for the measurement of two localized plantar pressures. The sensors (22A, 22B, 24A, 24B) are operable to measure the weight transfer along the foot as the individual moves which may be combined with other sensors (26) such as kinematic sensors to measure the angular speed of body segments of the lower extremities and kinematic sensors to measure the angle of the prosthesis (14) knee joint.

Each sensor (22A, 22B, 24A, 24B) may comprise a thin Force-Sensing Resistor (FSR) polymer cell directly connected to the interface (30) of the control system (100) or indirectly using an intermediary system (not shown), for instance a wireless emitter. Of course, other types of communication link technologies may be used, such as, for example, optical. The FSR cell has a decreasing electrical resistance in response to an increasing force applied perpendicularly to the surface thereof. Each cell outputs a time variable electrical signal for which the intensity is proportional to the total vertical plantar pressure over its surface area. The size and position of the plantar pressure sensors (22A, 22B, 24A, 24B) may be defined in accordance with the stability and the richness (intensity) of the localized plantar pressure signals provided by certain underfoot areas during locomotion. For example, it was found by experimentation that the heel and the toe regions are two regions of the foot sole where the Plantar Pressure Maximum Variation (PPMV) may be considered as providing a signal that is both stable and rich in information.

Accordingly, the controller (40) may use the data signals from the four localized plantar pressure sensors (22A, 22B, 24A, 24B), as well as the information gathered from the data signals of the other sensors (26) such as kinematic sensors, in order to decompose the locomotion of the individual (10) into a finite number of states, and generate the appropriate control signals for controlling the actuating mechanism (16) according to the locomotion. Of course, the controller (40) is not limited to the use of the preceding data signals.

An example of a controller (40) and control system (100) using sensors comprising plantar pressure sensors as well as kinematic sensors is described in U.S. patent application Ser. No. 10/600,725 filed Jun. 20, 2003, entitled "CONTROL SYSTEM AND METHOD FOR CONTROLLING AN ACTUATED PROSTHESIS", by Stéphane Bédard, the entire disclosure of which is hereby incorporated by reference herein.

Figure 3:
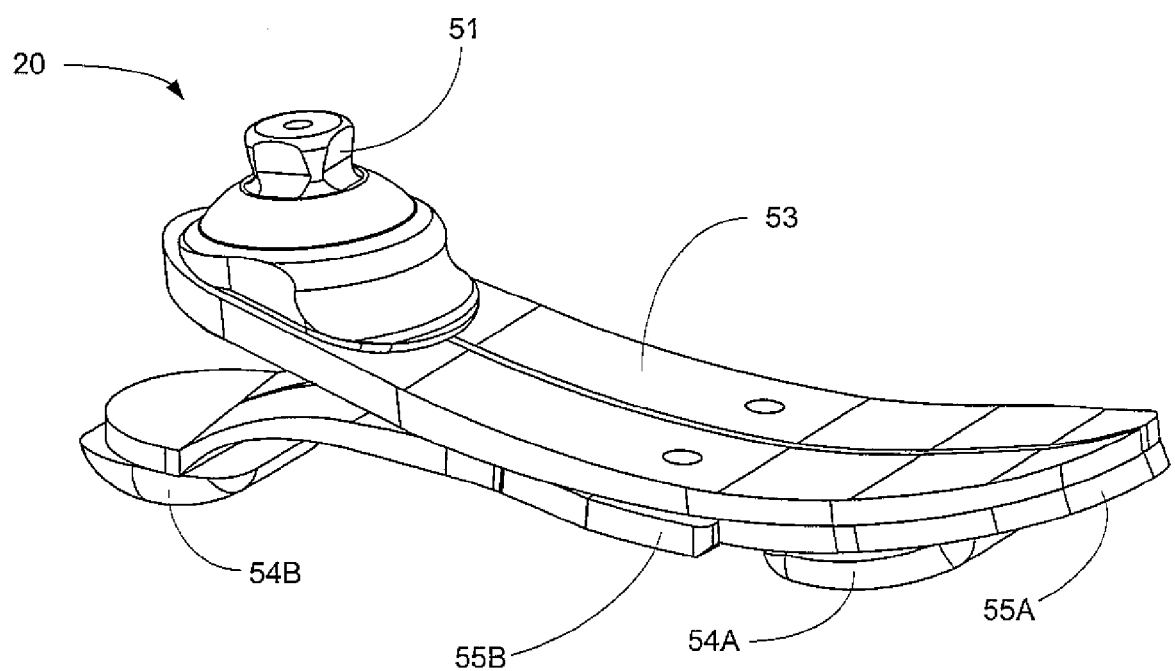
FIG. 3 is a perspective view, from the front and slightly above, of a instrumented prosthetic foot.
Figure 4:
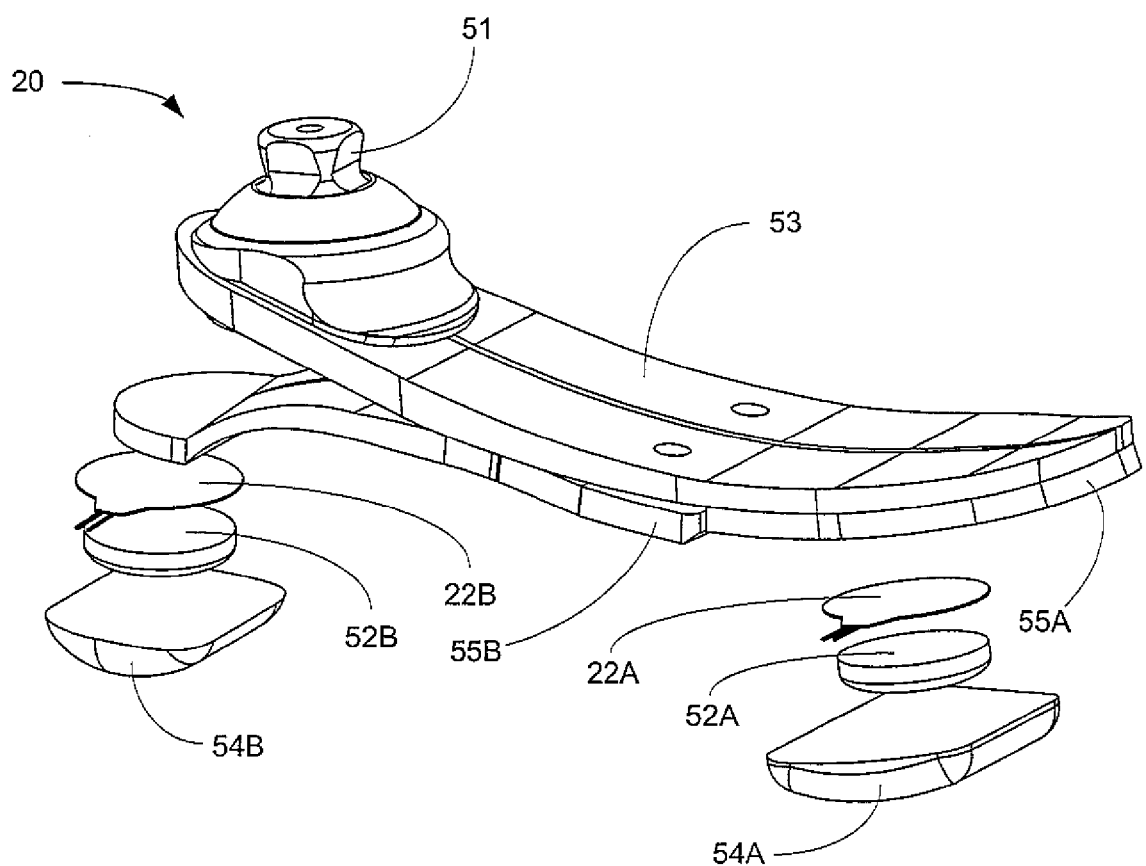
FIG. 4 is an exploded perspective view of the instrumented prosthetic foot of FIG. 3.

To facilitate the acquisition of the data in a repeatable and dependable manner, the sensors (22A, 22B) are incorporated in to the structure of the foot (20). An embodiment of the instrumented prosthetic foot (20) is shown in more detail in FIGS. 3 and 4. The instrumented prosthetic foot (20) includes a foot plate (53), forming an elongated body, with a connector (51) at one end, a toe plate (55A) and a heel plate (55B) that is cantilevered from the foot plate (53). Such an arrangement is provided by, for example, a Vari-Flex® prosthetic foot from Össur. Pressure sensors (22A, 22B) are located at longitudinally spaced locations on the underside of the foot plate (53) and heel plate (55) respectively. The sensors (22A, 22B) are covered by rigid plates (52A, 52B) and resilient pads (54A, 54B). The pressure sensors (22A, 22B) are located so as to be responsive to loads imposed on the instrumented prosthetic foot (20) at the regions corresponding to the toe area and the heel area respectively.

The rigid plates (52A, 52B) covering the sensors (22A, 22B), although not essential, help to optimize the pressure distribution on the entire surface of the sensors (22A, 22B) as well as inhibiting any shearing and may be made of 85 A durometer polyurethane. Of course, other type of material may be used as well.

The pads (54A, 54B) wrap up the rigid plates (52A, 52B) and the sensors (22A, 22B), forming a ground engaging member, in order to optimize the contact between the instrumented prosthetic foot (20) and the ground. The pads (54A, 54B) may be made of 40 A durometer polyurethane. Of course, other type of material may be used as well.

In operation, therefore, as the foot (20) traverses the ground, the force applied to the heel plate (55B) is measured by the sensor (22B) and a corresponding signal forwarded to the controller (40). The force applied to the toe plate (55A) is also measured by the sensor (22A) and the relative loading between the two locations is measured. As the foot (20) continues to traverse the ground, the force applied to the toe area increases and that at the heel decreases to provide a pair of signals from which the disposition of the leg may be determined and the appropriate control provided to the actuator (16).

Figure 5:
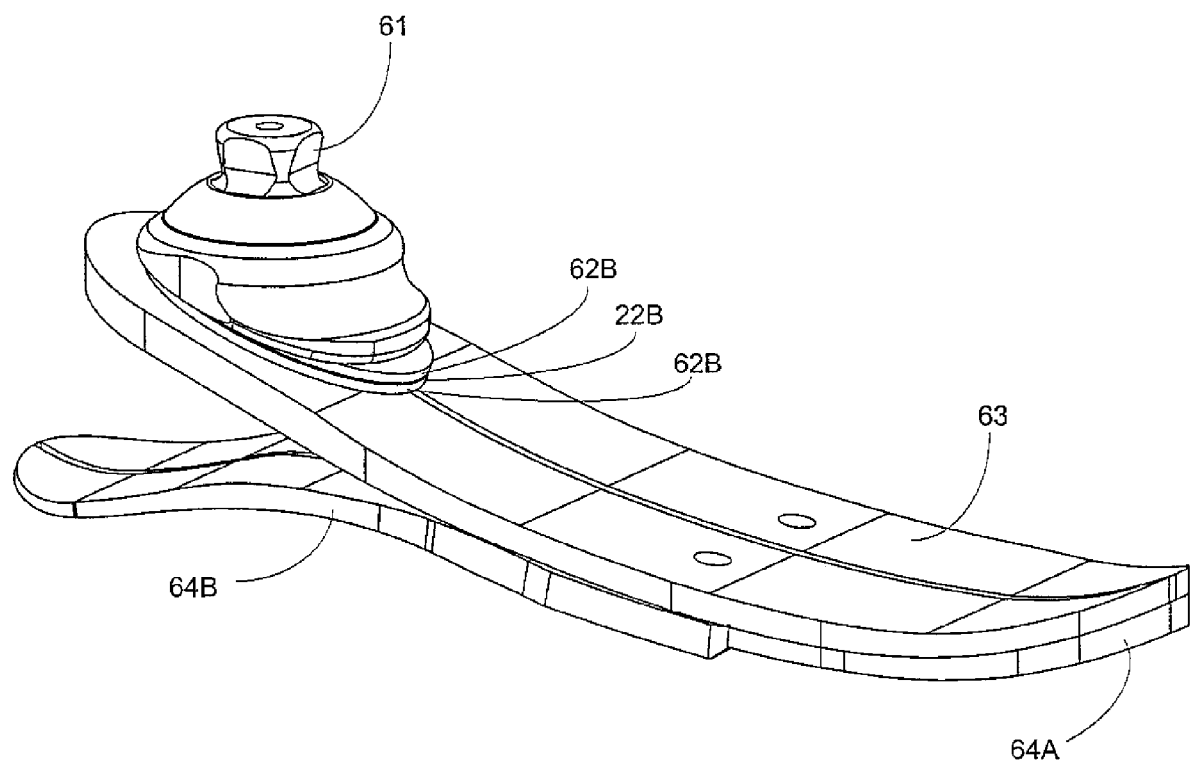
FIG. 5 is a perspective view, from the front and slightly above, of an alternative embodiment of the instrumented prosthetic foot of FIG. 3.
Figure 6:
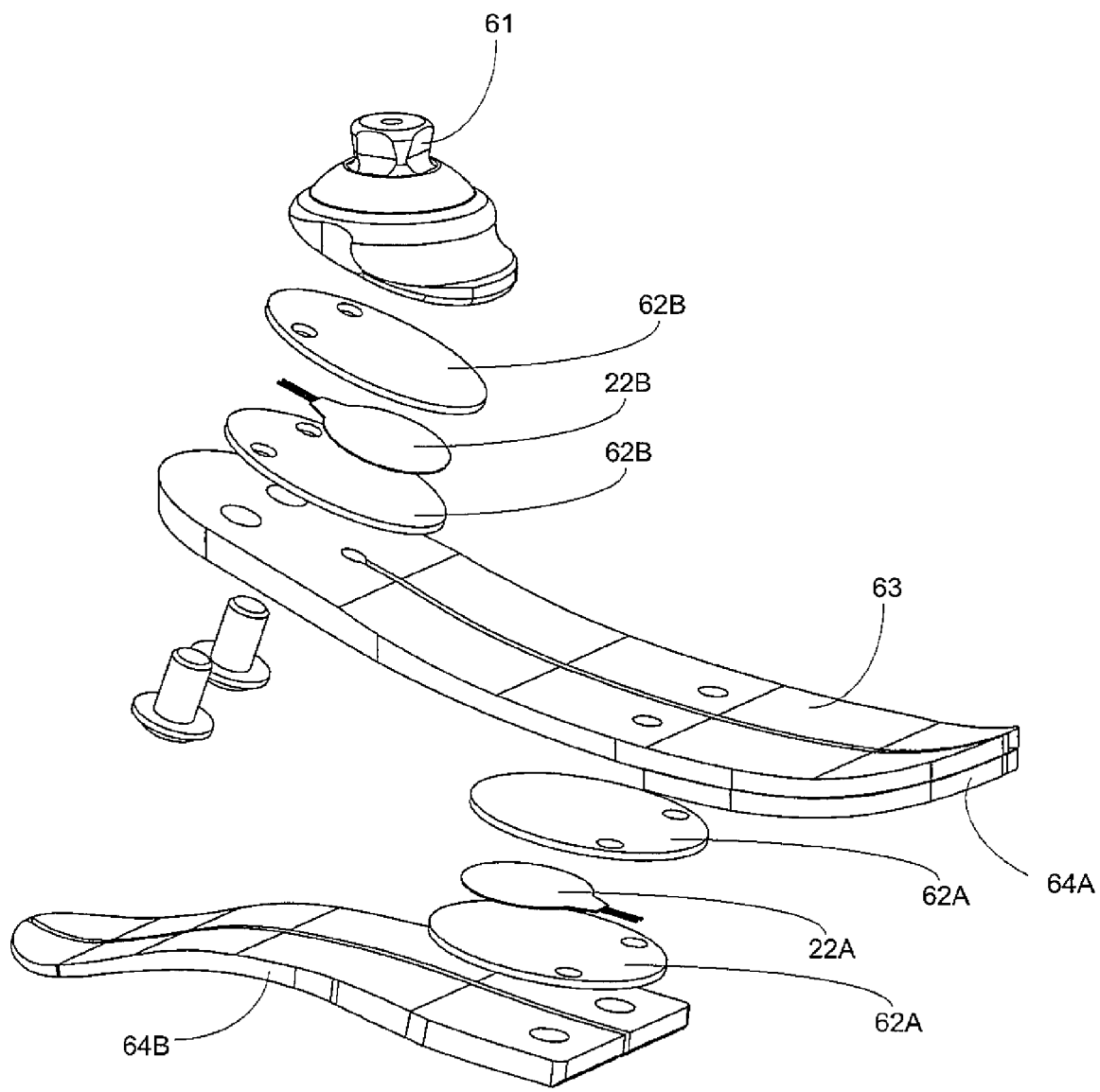
FIG. 6 is an exploded perspective view of the instrumented prosthetic foot of FIG. 5.

An alternative embodiment of the instrumented prosthetic foot (20) is shown in FIGS. 5 and 6. The instrumented prosthetic foot (20) includes connector (61), foot plate (63), toe plate (64A) and heel plate (64B), such as provided by, for example, a Vari-Flex® prosthetic foot from Össur. Pressure sensors (22A, 22B) are located between the foot plate (63)

and rigid plates (62A, 62B). The pressure sensors (22A, 22B) are located so as to be responsive to load imposed on the instrumented prosthetic foot (20) at the regions corresponding to the toe area and the heel area respectively. More specifically, pressure sensor (22A) is sandwiched between a pair of rigid plates (62A), which in turn are positioned between the heel plate (64B) and the foot plate (63). Pressure sensor (22B) is sandwiched between a pair of rigid plates (62B), which in turn are positioned between the foot plate (63) and the connector (61).

As for the previous embodiment, rigid plates (62A, 62B) covering the sensors (22A, 22B), although not essential, help to optimize the pressure distribution on the entire surface of the sensors (22A, 22B) as well as inhibiting any shearing and may be made of 85 A durometer polyurethane. Of course, other type of material may be used as well.

Figure 7:
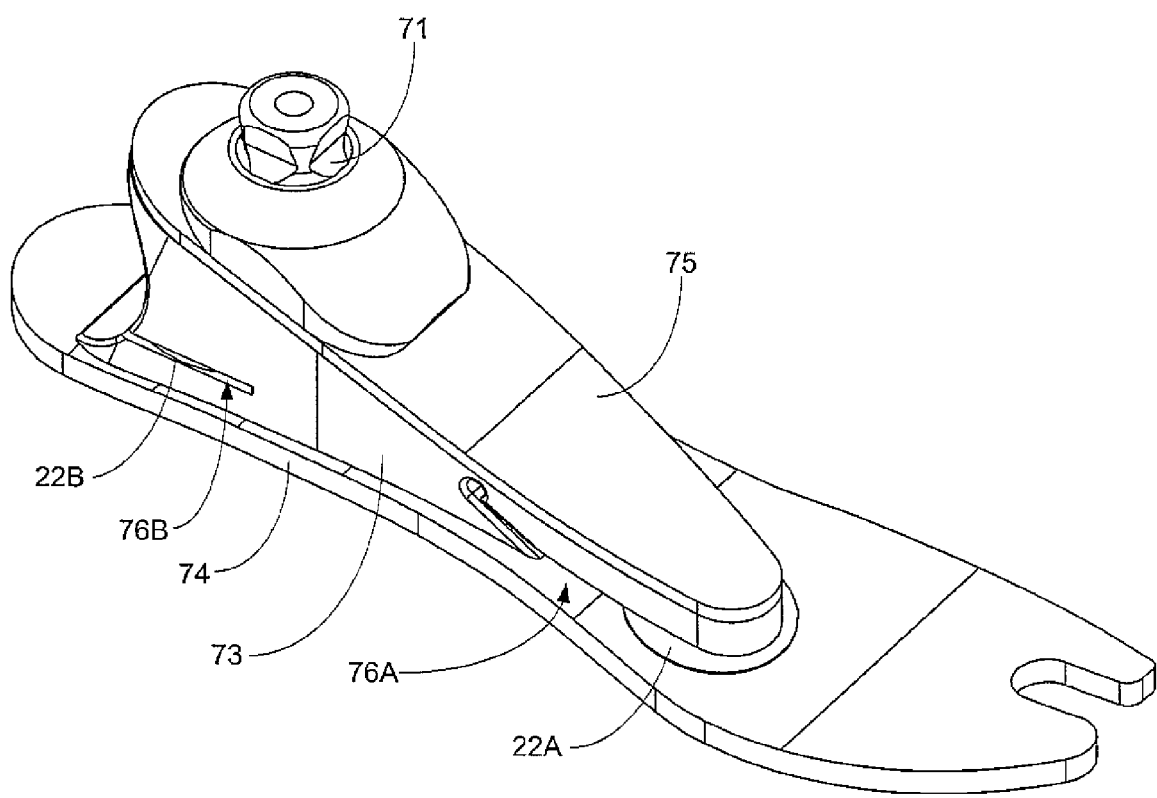
FIG. 7 is a perspective view, from the front and slightly above, of another alternative embodiment of the instrumented prosthetic foot of FIG. 3
Figure 8:
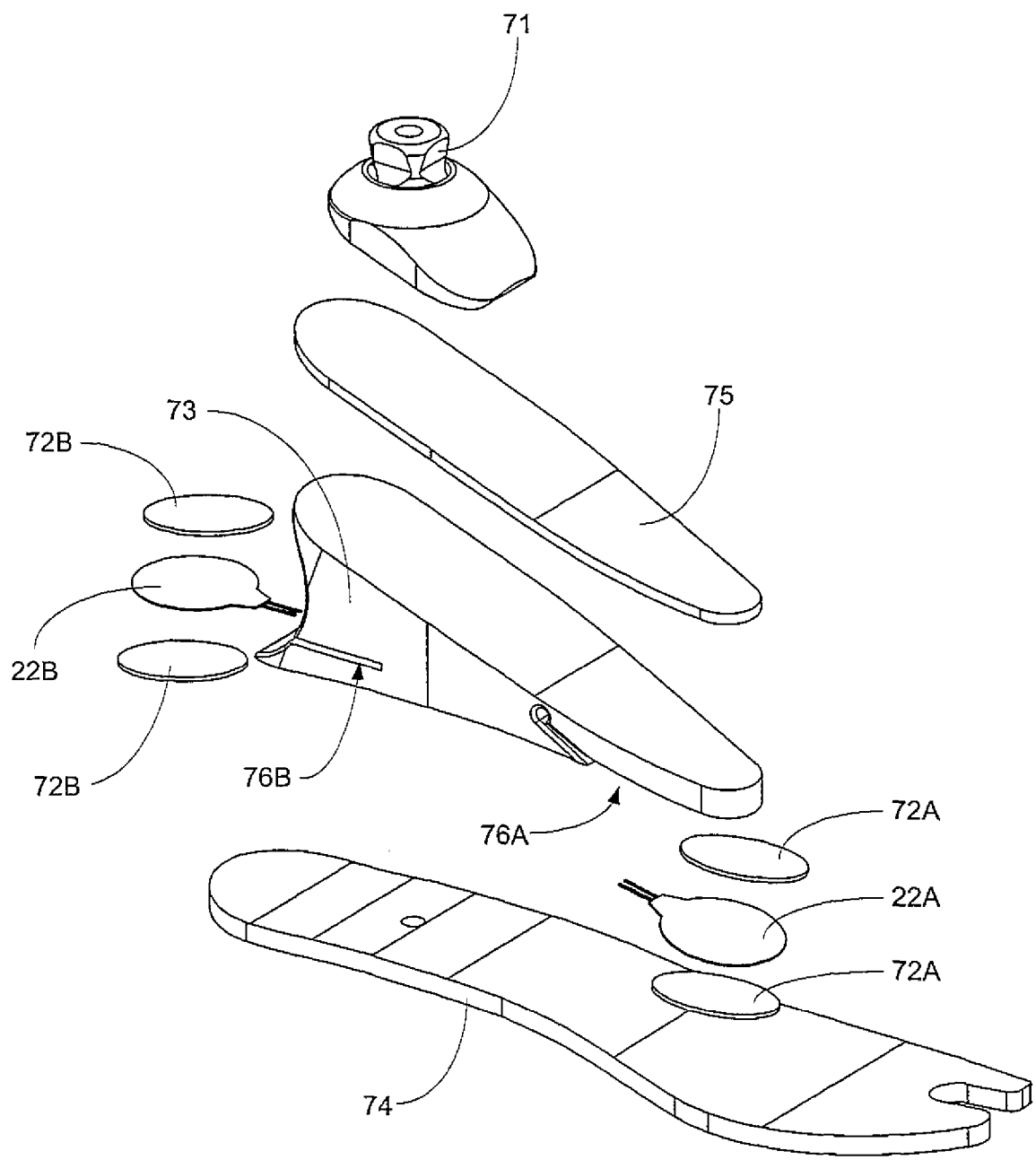
FIG. 8 is an exploded perspective view of the instrumented prosthetic foot of FIG. 7.

Another alternative embodiment of the instrumented prosthetic foot (20) is shown in FIGS. 7 and 8. The instrumented prosthetic foot (20) includes connector (71), top foot plate (75), foam cushion core (73) and bottom foot plate (74), such as provided by, for example, a LP Talux® prosthetic foot from Össur. Pressure sensors (22A, 22B) are sandwiched between pairs of rigid plates (72A, 72B). The pressure sensors (22A, 22B) are located so as to be responsive to load imposed on the instrumented prosthetic foot (20) at the regions corresponding to the toe area and the heel area respectively. More specifically, pressure sensor (22A) is sandwiched between a pair of rigid plates (72A), which in turn are positioned within gap (76A), which is located between a bottom foot plate (74) and a foam cushion core (73). Pressure sensor (22B) is sandwiched between a pair of rigid plates (72B), which in turn are positioned within gap (76B), which is located within the foam cushion core (73).

Again, as for the previous embodiments, rigid plates (72A, 72B) covering the sensors (22A, 22B), although not essential, help to optimize the pressure distribution on the entire surface of the sensors (22A, 22B) as well as preventing any shearing and may be made of 85 A durometer polyurethane. Of course, other type of material may be used as well.

Figure 9:
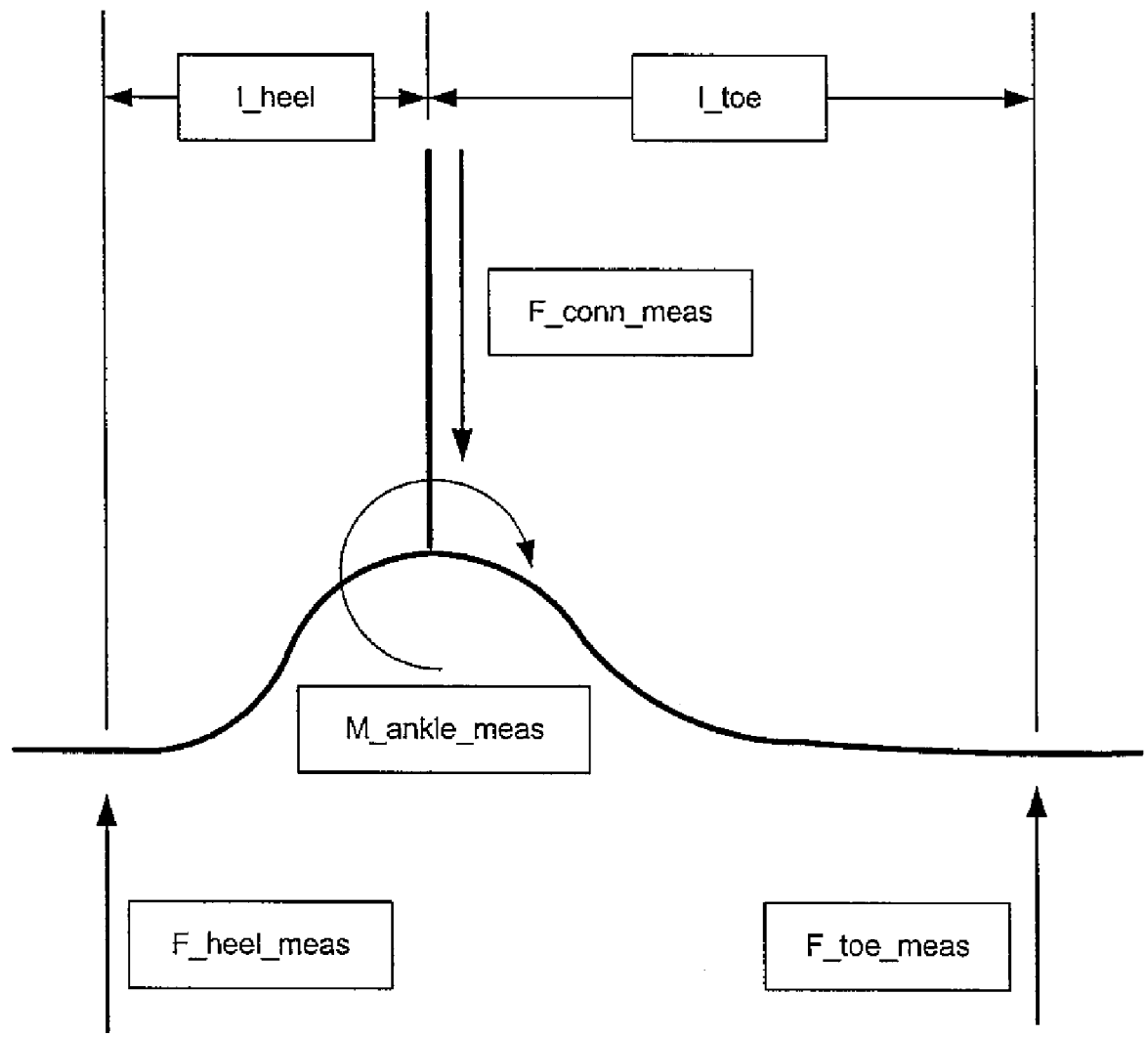
FIG. 9 is schematic view of forces exerted on a foot.

In the previous embodiments, the force (or pressure) at the toe and heel areas, F_toe and F_heel respectively, was obtained by positioning pressure sensors (22A, 22B) directly at those areas. More specifically, referring to FIG. 9, F_toe and F_heel were obtained as follows:

$$F\_toe = F\_toe\_meas \qquad \text{Equation 1}$$

$$F\_heel = F\_heel\_meas \qquad \text{Equation 2}$$

In other possible embodiments of the instrumented prosthetic foot (20), sensors (22A, 22B) may not be restricted to being positioned directly at the toe and heel areas, the equivalent information may be obtained by measuring the equivalent torque at the ankle and the axial force at the connector of the instrumented prosthetic foot (20). F_toe and F_heel may be defined in terms of the torque measured at the ankle, M_ankle_meas, and the force measured at the connector, F_conn_meas, using the following equations:

$$F\_toe = \frac{M\_ankle\_meas + (F\_conn\_meas \cdot I\_heel)}{(I\_heel + I\_toe)} \qquad \text{Equation 3}$$

$$F\_heel = \frac{M\_ankle\_meas + (F\_conn\_meas \cdot I\_toe)}{(I\_heel + I\_toe)} \qquad \text{Equation 4}$$

where
I_heel is the distance between the center of the connector and the center of the heel area;
I_toe is the distance between the center of the connector and the center of the toe area.

Figure 10:
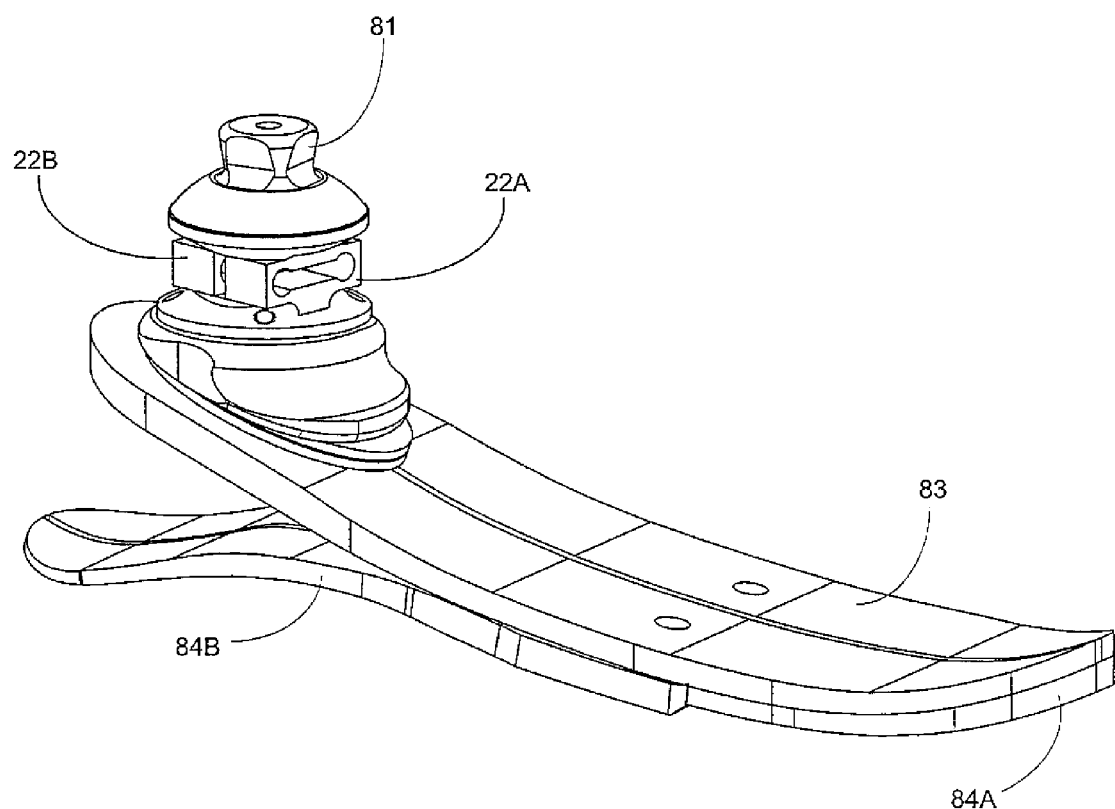
FIG. 10 is a perspective view, from the front and slightly above, of a further still alternative embodiment of the instrumented prosthetic foot of FIG. 3
Figure 11:
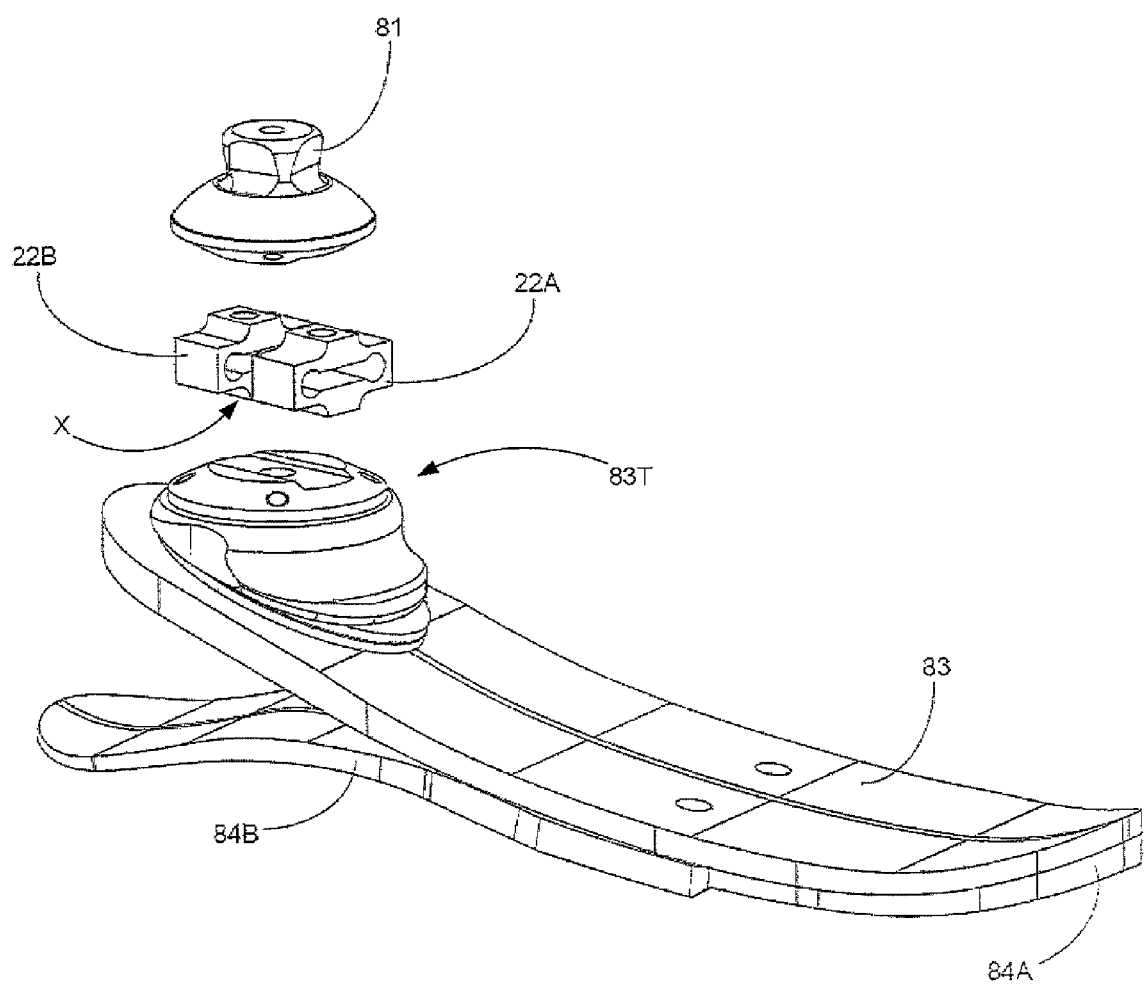
FIG. 11 is an exploded perspective view of the instrumented prosthetic foot of FIG. 10.

Following the previous discussion about the locations of sensors (22A, 22B), a further alternative embodiment of the instrumented prosthetic foot (20) is shown in FIGS. 10 and 11. The instrumented prosthetic foot (20) includes connector (81), an elongated body or foot plate (83), toe plate (84A) and heel plate (84B), such as provided by, for example, a Vari-Flex® prosthetic foot from Össur, and load cells (22A, 22B). Load cells (22A, 22B) are located below connector (81), load cell (22A) being slightly biased towards the toe area of the foot and load cell (22B) being slightly biased towards the heel area. The pair of load cells (22A, 22B) are positioned side by side and interposed between the connector (81) and the top part (83T) of the elongated body (83) and as such serve to both connect the foregoing together and to measure the load on the connector (81). The side by side load cells (22A, 22B) are in close proximity to one another and free of any load bearing element therebetween (area X in FIG. 11). In this way, the load cells (22A, 22B) support essentially the full load on the connector (81). As is known in the art, load cells are deformable (i.e. flexible, compressible and resilient). Therefore, the load cells (22A, 22B) are so deformed by the above-mentioned full load as to provide a multidirectional movement of the connector (81) relative to the elongated body (83). The foregoing is due to the fact that there is no other load bearing element between the load cells (22A, 22B), as is shown in area X, and the deformable nature of the load cells (22A, 22B) which allow the connector (81) to move in multiple directions relative to the elongated body (83). Thus, by not including any other load bearing element between the side by side proximate load cells 22A, 22B), these load cells 22A, 22B) can measure the load on the connector (81) during movement thereof in any direction including in the sagittal plane, in the coronal plane and/or in any plane between the both representing complex directions included into the corano-sagittal plane. Since the sensors (22A, 22B) are not located directly at the toe and heel areas, Equation 3 and Equation 4 may be used, for example by controller (40), to compute the equivalent pressures at the toe and heel areas by defining the equivalent torque at the ankle and the axial force at connector (81) as follows:

$$F\_conn\_meas = F\_22B + F\_22A \qquad \text{Equation 5}$$

$$M\_ankle\_meas = F\_22B \cdot I\_22B - F\_22A \cdot I\_22A \qquad \text{Equation 6}$$

where
F-22B is the force measured at sensor 22B;
F-22A is the force measured at sensor 22A;
I-22B is the distance between the center of the connector (81) and the center of sensor 22B;
I-22A is the distance between the center of the connector (81) and the center of sensor 22A.

Figure 12:
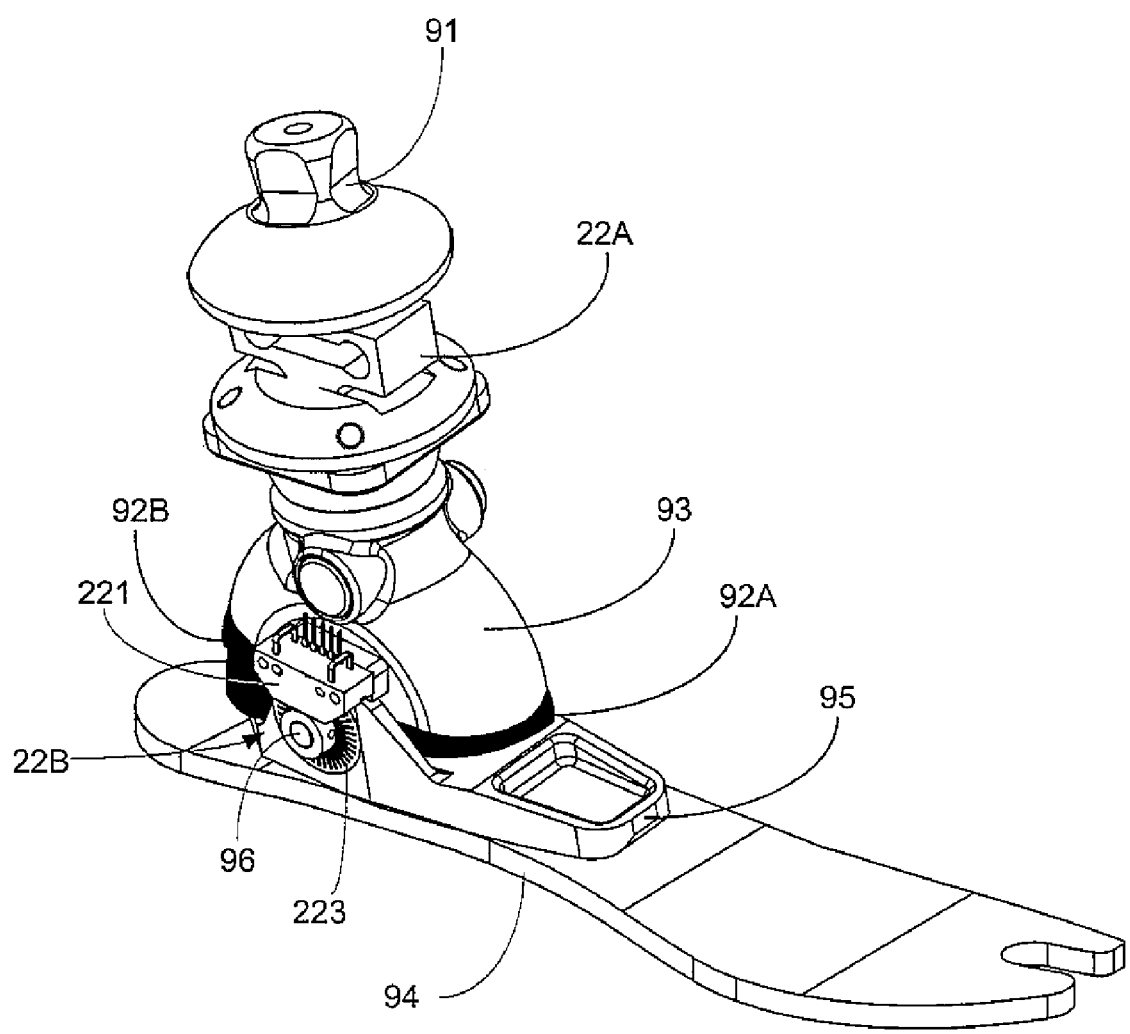
FIG. 12 is a perspective view, from the front and slightly above, of a yet further still alternative embodiment of the instrumented prosthetic foot of FIG. 3
Figure 13:
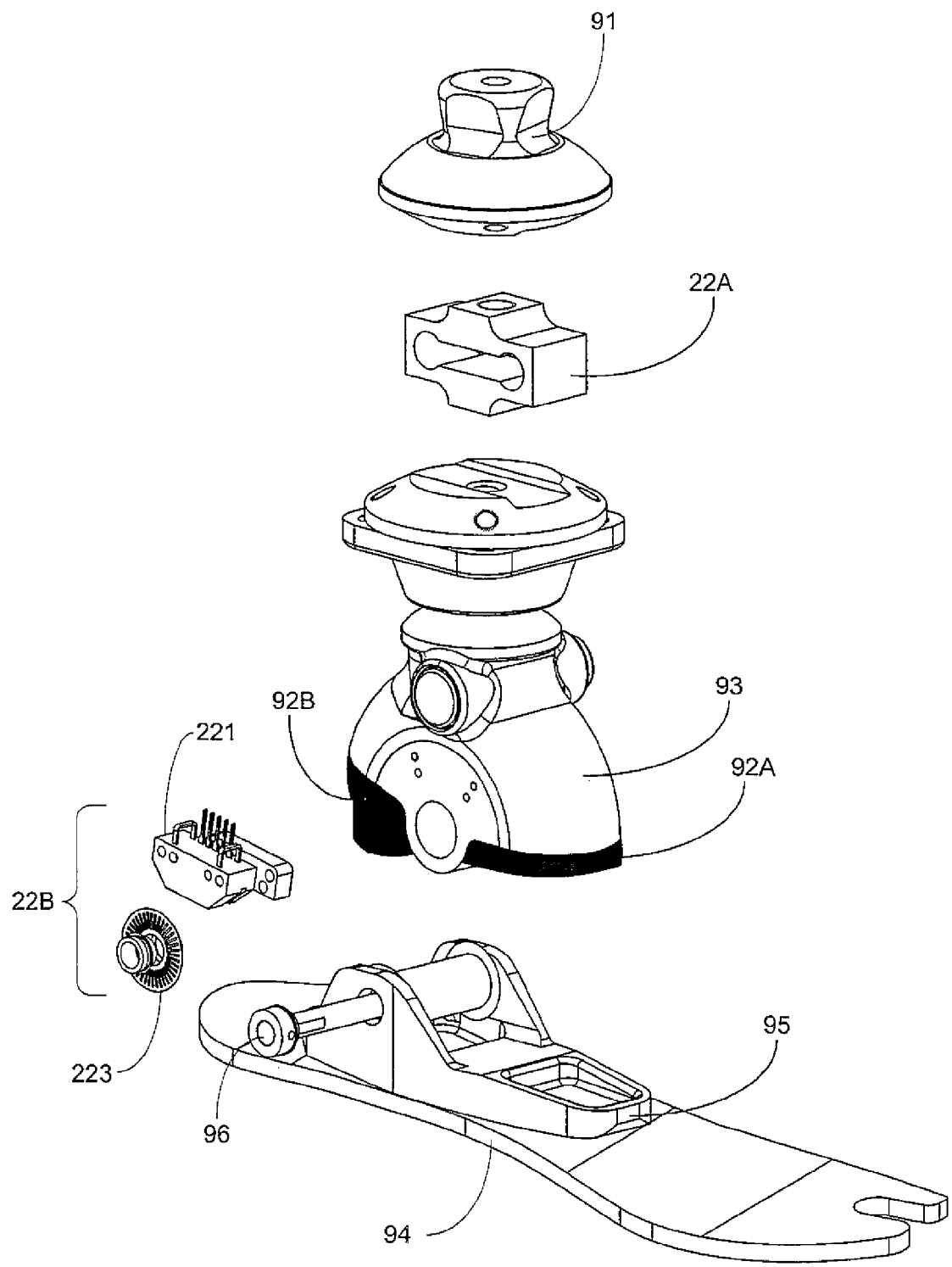
FIG. 13 is an exploded perspective view of the instrumented prosthetic foot of FIG. 12.

In the previous embodiments of the instrumented prosthetic foot (20), the force (or pressure) at the toe and heel areas, F_toe and F_heel respectively, was obtained either by positioning pressure sensors (22A, 22B) directly at those areas or by positioning pressure sensors or load cells (22A, 22B) in other areas and obtaining the equivalent information by computing the equivalent torque at the ankle and the axial force at the connector. Other types of sensors may also be used to obtain the equivalent torque at the ankle and the axial force at the connector. Such an example is illustrated by a further still embodiment of the instrumented prosthetic foot (20), which is shown in FIGS. 12 and 13. The instrumented prosthetic foot (20) includes connector (91), mounted on pivoting ankle (93). Bumpers (92A, 92B) are positioned between the pivoting ankle (93) and rocker plate (95) located on a foot plate (94). The pivoting ankle (93) is connected to the rocker plate (95) by a pivot pin (96). Such an arrangement is provided by, for example, an Elation® prosthetic foot from Össur. A load cell (22A) and an optical encoder (22B) are incorporated into the foot (20) to provide measurement of the distribution of forces along the foot (20). Load cell (22A) is positioned between connector (91) and pivoting ankle (93). Optical encoder (22B) comprises reader (221) and disk (223). Reader (221) is located on pivoting ankle (93) while disk (223) is located on rocker plate (95) and encircles pivot pin (96). Once again, Equation 3 and Equation 4 may be used, for example by controller (40), to compute the equivalent pressures at the toe and heel areas by defining the equivalent torque at the ankle and the axial force at connector (91) as follows:

$$F\_conn\_meas = F\_22A \quad \text{Equation 7}$$

$$M\_ankle\_meas = R\_ankle\_meas \cdot R\_const \quad \text{Equation 8}$$

where

F-22A is the force measured at sensor 22A;

R_ankle_meas is the rotation measurement of pivoting ankle (93) about pivot pin (96) as measured by optical encoder (22B);

R_const is a constant associated with the resistance of bumpers (92A, 92B) to compression, which constant varies depending in the material used.

Figure 14:
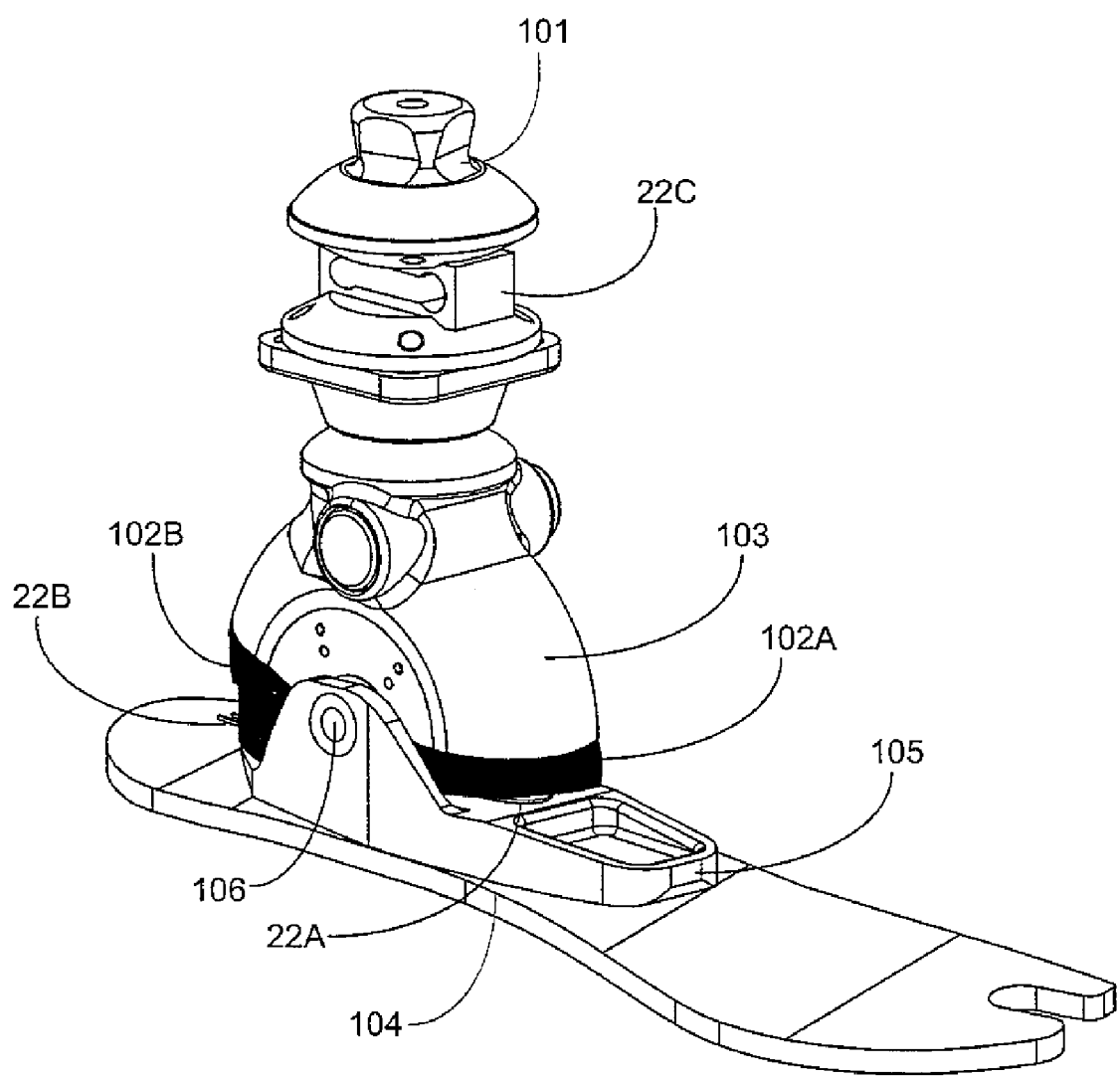
FIG. 14 is a perspective view, from the front and slightly above, of a further alternative embodiment of the instrumented prosthetic foot of FIG. 3
Figure 15:
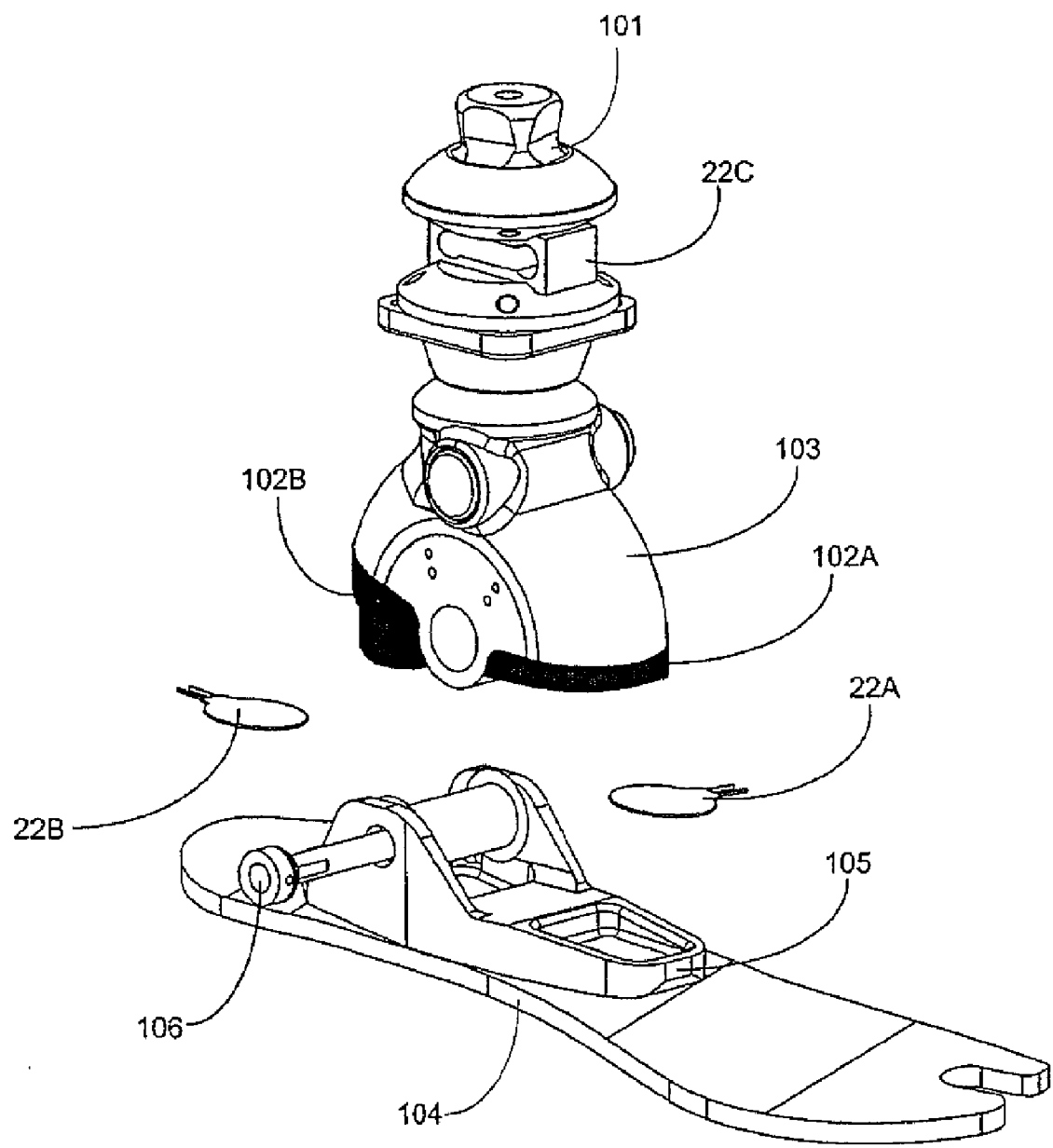
FIG. 15 is an exploded perspective view of the instrumented prosthetic foot of FIG. 14.

A yet further alternative embodiment of the instrumented prosthetic foot (20) is shown in FIGS. 14 and 15. The instrumented prosthetic foot (20) includes connector (101), mounted on pivoting ankle (103). Bumpers (102A, 102B) are positioned between the pivoting ankle (103) and rocker plate (105) located on a foot plate (104). The pivoting ankle (103) is connected to the rocker plate (105) by a pivot pin (106). Such an arrangement is provided by, for example, an Elation® prosthetic foot from Össur. Pressure sensors (22A, 22B) and load cell (22C) are incorporated into the foot (20) to provide measurement of the distribution of forces along the foot (20). Pressure sensor (22A) is positioned between rocker plate (85) and bumper (82A) while pressure sensor (22B) is positioned between rocker plate (85) and bumper (82B). A load cell (22C) is positioned between connector (91) and pivoting ankle (93).

In this embodiment, Equation 6 is used to compute the equivalent torque at the ankle, while the axial force at connector (101) is computed using the following equation:

$$F\_conn\_meas = F\text{-}22C \quad \text{Equation 9}$$

Load cell (22C) is required to compute the axial force at connector (101) since when there is no torque at the ankle, i.e. the wearer of the prosthesis is standing still, the axial force is being exerted in its entirety onto pivot pin (96).

In all of the described embodiments, the sensors (22A, 22B) may be directly connected to interface (30) of control system (100) or indirectly using an intermediary system (not shown), for instance a wireless emitter. Of course, other types of communication link technologies may be used, such as, for example, optical.

Other types of non-articulated or articulated prosthetic foot may be used as well as long as the selected prosthetic foot provides approximately the same dynamical response as the ones mentioned here above. Nevertheless, an articulated foot offers the best performances. The instrumented prosthetic foot (20) may further have an exposed metal or composite structure or it may have a cosmetic covering that gives it the appearance of a human ankle and foot.

It should be noted that the present invention is not limited to its use with the mechanical configuration illustrated in FIG. 1 or the control system (100) illustrated in FIG. 2. It may be used with a leg prosthesis having more than one joint. For instance, it may be used with a prosthesis having an ankle joint, a metatarsophalangeal joint or a hip joint in addition to a knee joint. Moreover, instead of a conventional socket a osseo-integrated devices could also be used, ensuring a direct attachment between the mechanical component of the prosthesis and the amputee skeleton. Other kinds of prostheses may be used as well.

What is claimed is:

1. An instrumented prosthetic foot for use with an actuated leg prosthesis controlled by a controller, the instrumented prosthetic foot comprising:

an elongated body having a top and a bottom part;

a connector to connect the instrumented prosthetic foot to the leg prosthesis; and a pair of load sensors interposed between and interconnecting the connector and the top part of the elongated body and positioned side by side, the pair of load sensors being configured to measure the load on the connector;

wherein the pair of load sensors are free of any other load bearing element therebetween so as to support essentially the full load between the connector and the elongated body, and to be deformable thereby as to provide for multidirectional movement of the connector relative to the elongated body thereby sensing the load during movement in any direction, the sensors being in communication with the controller, and a first sensor and a second sensor of the pair of sensors being arranged to sense and communicate a signal indicative of an applied load at a heel region and toe region of the elongated body, respectively.

2. An instrumented prosthetic foot according to claim 1, wherein the pair of load sensors are in close proximity to one another.

3. An instrumented prosthetic foot according to claim 1, wherein:

the first sensor of the pair of sensors being slightly biased towards the heel region of the elongated body and the second sensor of the pair of sensors being slightly biased towards the toe region of the elongated body.

4. An instrumented prosthetic foot according to claim 1, wherein:

the pair of sensors arranged to transmit signals to the controller using a wired connection.

5. An instrumented prosthetic foot according to claim 1, wherein:

the pair of sensors arranged to transmit signals to the controller using a wireless connection.

6. An instrumented prosthetic foot according to claim 1, wherein:

the connector removably connects the instrumented prosthetic foot to the leg prosthesis.

* * * * *